(12) United States Patent
Furman et al.

(10) Patent No.: US 7,826,049 B2
(45) Date of Patent: Nov. 2, 2010

(54) INSPECTION TOOLS SUPPORTING MULTIPLE OPERATING STATES FOR MULTIPLE DETECTOR ARRANGEMENTS

(75) Inventors: Dov Furman, Rehovot (IL); Ehud Tirosh, Mevaseret Zion (IL); Shai Silberstein, Rehovot (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 310 days.

(21) Appl. No.: 12/142,416

(22) Filed: Jun. 19, 2008

(65) Prior Publication Data
US 2009/0201494 A1 Aug. 13, 2009

Related U.S. Application Data

(60) Provisional application No. 61/027,586, filed on Feb. 11, 2008.

(51) Int. Cl.
*G01N 21/00* (2006.01)
(52) U.S. Cl. .................. 356/237.5; 356/237.4
(58) Field of Classification Search .......... None
See application file for complete search history.

(56) References Cited

U.S. PATENT DOCUMENTS

| | | | |
|---|---|---|---|
| 5,699,447 | A | 12/1997 | Alumot et al. |
| 6,366,315 | B1 | 4/2002 | Drescher |
| 6,608,676 | B1 | 8/2003 | Zhao et al. |
| 6,693,664 | B2 | 2/2004 | Neumann |
| 6,724,473 | B2 | 4/2004 | Leong et al. |
| 7,088,443 | B2 | 8/2006 | Vaez-Iravani et al. |
| 7,265,900 | B2 | 9/2007 | Korngut et al. |
| 7,274,444 | B2 | 9/2007 | Furman et al. |
| 2002/0044278 | A1 | 4/2002 | Le |
| 2004/0012775 | A1 | 1/2004 | Kinney et al. |
| 2004/0146295 | A1 | 7/2004 | Furman et al. |
| 2006/0066843 | A1 | 3/2006 | Guetta et al. |
| 2007/0013898 | A1 | 1/2007 | Wolters et al. |
| 2007/0229813 | A1 | 10/2007 | Miyakawa et al. |
| 2007/0273945 | A1 | 11/2007 | Furman et al. |
| 2008/0037933 | A1 | 2/2008 | Furman et al. |
| 2008/0137074 | A1 | 6/2008 | Furman et al. |

OTHER PUBLICATIONS

Applied Materials South East Asia PTE. LTD.; PCT/IL2009/000572 Filed Jun. 9, 2009; International Search Report and Written Opinion; ISA/EP; mailed Sep. 16, 2009; 16 pp.

*Primary Examiner*—Gregory J Toatley, Jr.
*Assistant Examiner*—Amanda H Merlino
(74) *Attorney, Agent, or Firm*—Sonnenschein Nath & Rosenthal LLP

(57) ABSTRACT

An inspection system can support operation in multiple states. For instance, when inspecting an article, such as a semiconductor wafer, the tool can switch between imaging multiple locations using respective detectors to another operating state wherein multiple detectors operating in multiple imaging modes inspect a single location. An inspection system may combine the use of multiple detectors for multiple locations and the use of multiple viewing angles or modes for the same locations and thereby achieve high throughput. The different imaging modes can comprise, for example, different collection angles, polarizations, different spectral bands, different attenuations, different focal positions relative to the wafer, and other different types of imaging.

27 Claims, 9 Drawing Sheets

INSPECTION TOOLS SUPPORTING MULTIPLE OPERATING STATES FOR MULTIPLE DETECTOR ARRANGEMENTS

PRIORITY CLAIM

This application claims priority to U.S. Provisional Patent Application No. 61/027,586, filed Feb. 11, 2008 and entitled INSPECTION TOOLS SUPPORTING MULTIPLE OPERATING STATES FOR MULTIPLE DETECTOR ARRANGEMENTS, which is hereby incorporated by reference herein in its entirety.

BACKGROUND

Many electro-optical semi-conductor inspection systems contain at least two detectors.

One way of arranging these detectors is where every detector views a respective part of the inspected article. For example, U.S. Pat. No. 6,693,664 includes a discussion of an arrangement where there are multiple 2-dimensional detectors which are located at the focal plane of the system's imager to creating a continuous imaging surface. U.S. Pat. No. 7,274,444 includes discussion of an embodiment where the multiple 2-dimensional detectors are located with intervals between them.

An arrangement of line or TDI detectors may also be used, with special optics used so that the line detectors view areas that are side by side (see U.S. Pat. No. 6,366,315).

Another way to inspect articles is to let multiple detectors view the same location in the article, but with different imaging modes. U.S. Pat. No. 7,265,900, for example, discusses an embodiment in which all the detectors view the same area in a wafer but with different collection angles.

SUMMARY

An inspection system configured in accordance with one or more aspects of the present subject matter may be more useful and versatile than existing tools by supporting operation in multiple states. For instance, when inspecting an article, such as a semiconductor wafer, the tool can switch between imaging multiple locations using respective detectors to another operating state wherein multiple detectors image the same location in different imaging modes.

An inspection system may combine the use of multiple detectors for multiple locations and the use of multiple viewing angles or modes for the same locations and thereby achieve high throughput with lower sensitivity and lower throughput with higher sensitivity as needed.

As discussed further below, an electro-optical inspection system can comprise at least two imaging detectors, an illumination system comprising one or more light sources, and a set of imaging optics that relays light from the imaged object to the imaging detectors. Namely, the imaging optics can be positioned on an optical path between the wafer (or other object under inspection) and the detectors. The tool can be configured to operate in at least two "states," with the state adjusted by varying the composition and/or arrangement of the imaging optics. The term "state" is used to avoid confusion with "mode," which is used to refer to how the locations are imaged (i.e. imaging mode).

In a first state, (referred to as "multiple location state" below), at least two of the imaging detectors are used to view different physical locations on the article being inspected. The locations may partially overlap or may be completely separated. In the second state (referred to as "multiple imaging state" below), at least two of the imaging detectors view the same location on the article, but with different imaging modes (such as different collecting angles, for example).

Before inspection, according to a manual and/or automatic decision, the state of the inspection apparatus is changed using mechanical, electrical, optical and/or electro-optical control. For example, an operator could select a desired state, or the state could be specified as part of an inspection recipe. At least some of the detectors that are used for imaging when the tool is in the first state are also used for imaging when the tool is in the second state. In some embodiments, all of the detectors that are used for imaging when the tool is in the first state are also used for imaging when the tool is in the second state. Furthermore, some (or all) of the detectors used for imaging when the tool is in the second state are used for imaging when the tool is in the first state.

Put another way, detectors available for use by the tool may be treated as a set and categorized in a first subset if used for imaging in the first state and a second subset if used for imaging the second state. The sets may partially overlap, i.e. some detectors may be used in both states while some detectors are used only in one state. Alternatively, the subsets may fully overlap, with all the detectors used in the first state also used in the second state.

The detectors may comprise any suitable type. For example, in some embodiments, one or more detectors are two-dimensional (i.e. matrix) detectors. In some embodiments, one or more detectors are time delay integration (TDI) detectors. One or more detectors are line detectors in certain embodiments. In yet other embodiments, one or more detectors are photomultiplier tube (PMT) detectors, or may comprise avalanche photodiode detectors.

In some embodiments, some or all of the detectors are repositionable, and the tool is configured to reposition the detectors when changing between the first and second state. Further, the set of variable imaging optics can comprise a plurality of changeable filter elements and a splitting apparatus. In the first state, the splitting apparatus can direct light corresponding to different physical locations of the object under inspection along different optical paths, with each different optical path leading to a respective detector. In the second state, the changeable filter elements can be positioned in appropriate optical paths after the splitting apparatus in order to change the imaging mode of the detector in the path.

Examples of changeable filter elements include, but are not limited to, spatial masks, polarizers, spectral filters, attenuators, or elements (e.g. lens) that change the focus position of the detector relative to the surface of the object under inspection. For example, the objective lens may be focused at a particular point relative to the surface of the object under inspection. One or more changeable filters may adjust the focus of one detector so that light above, on, or below the focus point of the objective lens. Accordingly, different detectors may be focused at different points relative to the surface of the object.

As an example, in some embodiments, the inspection system comprises at least four detectors each operable to selectively image the object at least two modes. The modes may be selected by varying the imaging optics and/or may be a characteristic of the detectors themselves. In the first state, the system images at least four different locations on the object under inspection simultaneously, and in the second state, at least two locations on the object under inspection are imaged simultaneously in at least two modes. As another example, in the first state, the system images at least one location on the object under inspection simultaneously in two different modes.

A method of inspecting an object in an electro-optical inspection system comprising a set of detectors, the method can comprise illuminating the object, imaging at least one location on the object in different modes by using at least two detectors of a first subset of the detectors to image the same location, and imaging at least two different locations on the object, with each location imaged using a respective detector of a second subset of the detectors.

In some embodiments, the method can comprise repositioning at least some of the set of detectors between imaging the same location on the object in different modes and imaging at least two different locations on the object with a respective detector.

Certain embodiments of the method may include, splitting light along different optical paths so as to direct the light from respective locations on the object to the respective detectors when imaging at least two different locations with a respective detector. When imaging at least one location in multiple modes, the method can include positioning a plurality of changeable filter elements in the optical path leading to each detector to adjust the imaging mode of the detector.

In some embodiments in which light from the object is gathered using an objective lens, the method further comprises placing a post-objective lens configured to focus light from different physical locations on the object to respective detectors when imaging at least two different locations each with a respective detector, and replacing the post-objective lens with an optical element comprising multiple lenses so that multiple detectors image the same physical location on the object at different collection angles when the post-objective lens is in place.

In some embodiments in which an optical element in the path comprising multiple lenses is used, the method can comprise selectively placing one of a first and second objective lens in the optical path before the multi-lens optical element. Accordingly, when the first objective lens is in the optical path, the first objective lens and optical element in the path comprising multiple lenses direct light from different locations on the object to different respective detectors, and when the second objective lens is in the optical path, the second objective lens and optical element in the path comprising multiple lenses direct light so that at least two detectors image the same physical location on the object.

In some embodiments, the method comprises illuminating the object multiple times when using at least two detectors to image the same physical location on the object, with the illumination timed so that the respective detectors can image the location at different times.

In some embodiments, the method comprises changing between a state in which one or more locations are imaged in multiple modes to a state in which multiple locations are simultaneously imaged with different respective detectors. The state change can occur at any time. In embodiments in which inspection entails inspecting a plurality of slices extending along an imaging axis, the state can be changed in between slices.

BRIEF DESCRIPTION OF THE DRAWINGS

A full and enabling disclosure including the best mode of practicing the appended claims and directed to one of ordinary skill in the art is set forth more particularly in the remainder of the specification. The specification makes reference to the appended figures, in which:

DETAILED DESCRIPTION

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the instant disclosure includes modifications and variations as come within the scope of the appended claims and their equivalents. The use of headings, numberings, and the like is meant to assist the reader of the specification, and not to limit the subject matter.

Figure 9:
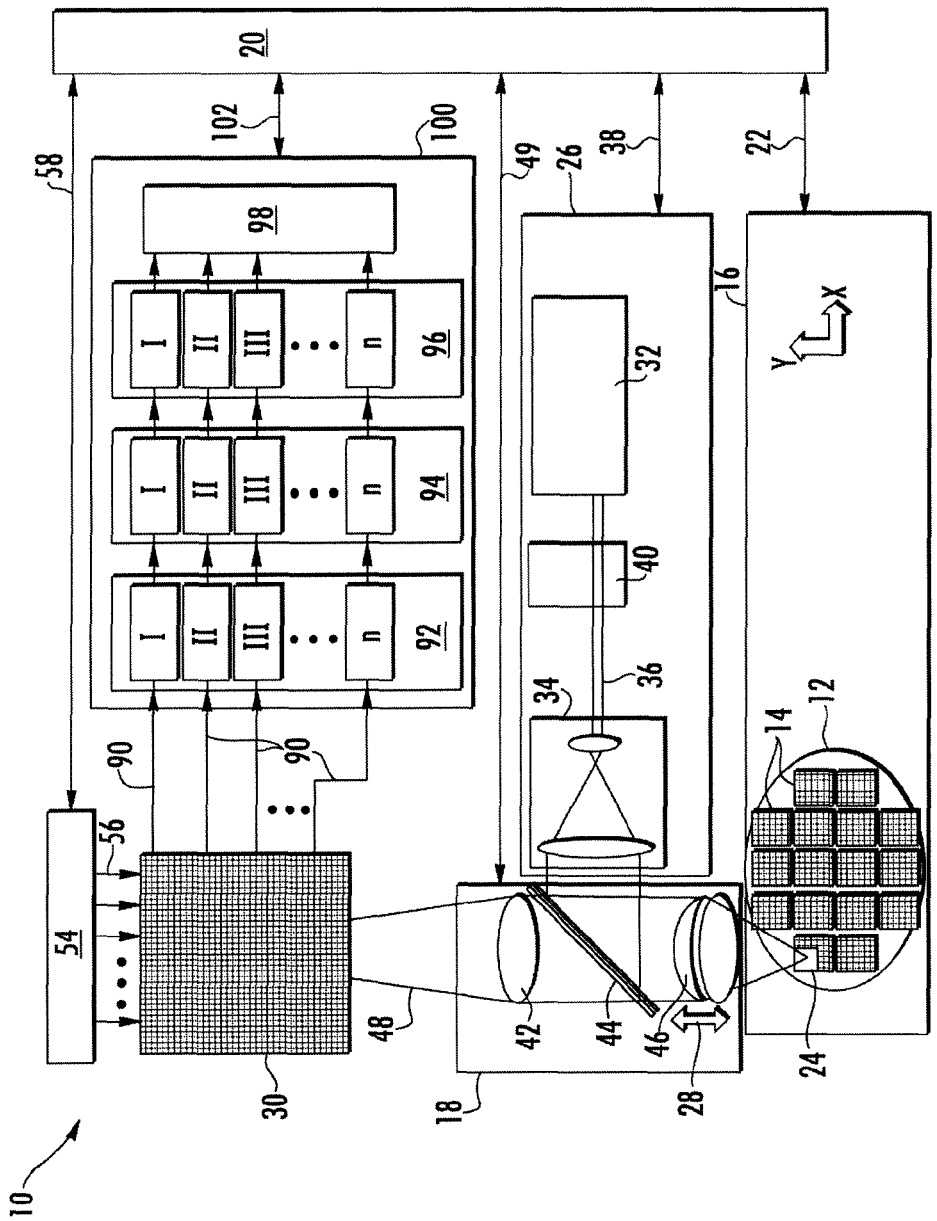
FIG. 9 is a block diagram showing illumination, imaging, and control components in an exemplary optical inspection tool.

Before discussing exemplary embodiments of detector arrangements for a multi-state tool, FIGS. 9 and 10 will be discussed to place the arrangements in context. FIG. 9 is a block diagram showing illumination, imaging, and control components in an exemplary optical inspection tool and FIG. 10 is a block diagram showing additional aspects of imaging and illumination in an exemplary optical inspection tool.

Figure 10:
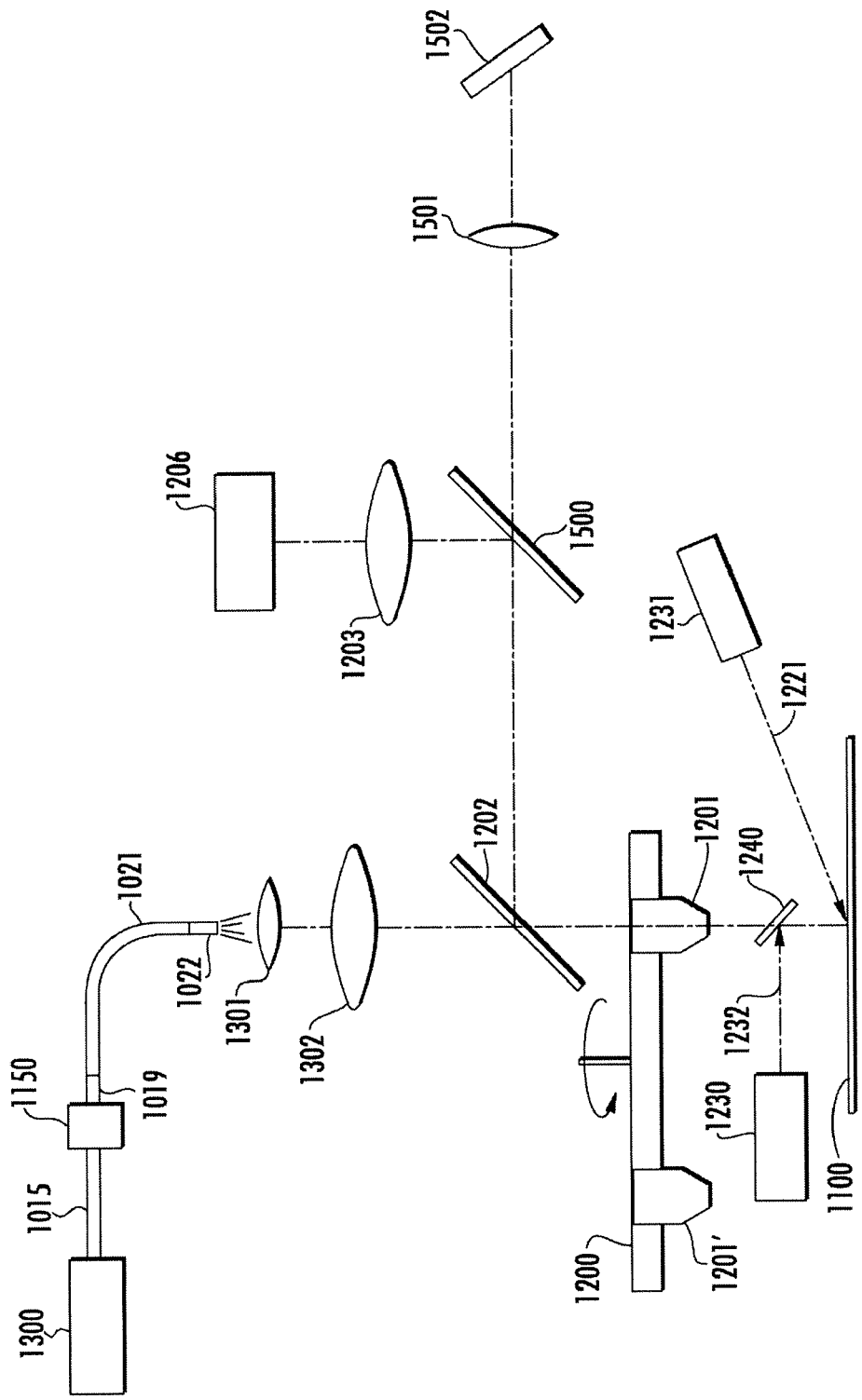
FIG. 10 is a block diagram showing additional aspects of imaging and illumination in an exemplary optical inspection tool Use of like reference numerals in different features is intended to illustrate like or analogous components.

In this example, FIG. 9 is a schematic diagram illustrating an exemplary embodiment of a system for fast on-line electro-optical detection of wafer defects, while FIG. 10 shows a schematic illustration of an object inspection system utilizing a laser source and a fiber optical delivery bundle in an exemplary inspection tool. For instance, the tool may comprise a Negevtech 3320, 3370, or other model optical inspection tool (available from Negevtech, Ltd. of Rehovot, Israel), modified to support one or more operating states in accordance with one or more aspects of the presently disclosed detector arrangements and methodologies.

Additional details regarding exemplary aspects of an optical inspection system can be found in U.S. patent application Ser. No. 10/345,097, published as US Patent Application No. 2004-0146295 A1, which is incorporated by reference herein for all purposes in its entirety to the extent it is not in conflict with the present subject matter. However, it is to be noted that the detector arrangement principles and multi-state tools discussed below can be used in any suitable inspection system that creates an image of an object at a focal plane.

As shown in FIG. 9, an inspection tool can include a focal plane assembly 30 comprising pixels from multiple two-dimensional detectors. Focal plane assembly 30 is configured so that light from an article being inspected is sensed by detectors arranged in accordance with one or more aspects discussed below so that the tool can support multiple operating states. In this example, assembly 30 is depicted as providing a continuous surface (this may be achieved by physically positioning the detectors near one another and/or by optically forming the surface). It will be recognized that, in different embodiments and depending on the optical configuration and state of the tool, a discontinuous surface may be presented in some instances.

In operation, the dies 14 of wafer 12 can be illuminated in any suitable manner, such as by laser light from pulsed illumination system 26. Light 48 represents rays of light scattered, reflected, and diffracted by the wafer. This light can be collected using imaging optics 18. In this example, imaging optics 18 comprise a beam splitter 44 (used in illuminating wafer 12 with light from laser system 26), focusing lens 42, and an objective lens 46 which may be adjusted using an auto-focus system 28 (not shown in detail). In this example, focusing lens 42 focuses light 48 onto focal plane assembly 30 and defines the focal plane of imaging optics 18. However, the actual content and arrangement of a particular set of imaging optics can vary. Particularly, the imaging optics 18 shown in this example are simplified for purposes of explaining general principles of an inspection tool. A tool that operates in multiple states can have more complex imaging optics configured in accordance with the present subject matter.

A patterned semiconductor wafer 12 featuring a plurality of wafer dies 14, is placed and aligned on a continuous moving XY translation stage 16 to impart motion between the wafer and the components used to image the wafer. XY translation stage 16 moves wafer 12 typically in a serpentine pattern beneath an optical imaging system 18, thereby changing which area of the wafer is in view of the imager. However, movement patterns other than a serpentine pattern could be used. Additionally, the wafer may be moved in a different manner in other embodiments. Furthermore, in some embodiments, the wafer may remain stationary, with apparent motion between the wafer and component(s) used to image the wafer imparted by the use of one or more optical components. For instance, a rotating mirror can be used to move the field of view of imaging optics 18 in a serpentine (or other) pattern across the wafer. In other embodiments, relative motion may be imparted by moving both the wafer and adjusting optical components.

Movement of XY translation stage 16 (and therefore movement of wafer 12) is synchronized with action of a multi-component camera system by a central control system 20 via control/data links 22, in such a way that wafer 12 moves the equivalent of one field of view 24 during a CCD matrix photo-detector frame time. For example, the frame time and motion may be synchronized so that the wafer moves only on the order of about $10^{-2}$ of a single pixel during exposure to an illumination system 26, thereby resulting in little to no image smear or loss of image resolution. Control system 20 can comprise any suitable type or arrangement of components used to orchestrate the inspection process, including, for example, a microprocessor-based controller, a general-purpose or specialized computer system, and the like.

In this example, illumination system 26 includes a repetitively pulsed laser 32, a laser beam expander 34, a laser beam light path 36, control/data links 38, and a crystal 40 having non linear optical properties and serving as a 'second harmonic' or 'third harmonic' generating crystal. This type of illumination system enables ultra fast imaging of a large field of view 24, by featuring pulsed laser 32 for repetitively generating and propagating a highly bright and highly energetic light pulse in an extremely short period of time. Illumination system 26 is in communication with the central control system 20 via control/data links 38. Of course, detector arrangements in accordance with the present subject matter can be used in any inspection system regardless of the particular type, mode, or manner of illumination.

Briefly, FIG. 10 illustrates exemplary components associated with illuminating an object in an inspection system. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination may be preferred. In order to detect a small particle on a surface, DF illumination can generally yield better results.

In bright field illumination in general, the illumination is incident on the sample through the same objective lens as is used for viewing the sample. FIG. 10 shows a bright field illuminating laser source 1300 delivering its output beam 1015 into an optical delivery fiber bundle 1021, preferably by means of a laser to fiber coupler 1150. This optical fiber bundle 1021 provides both uniform illumination on the sample and coherence breaking of the laser illumination. In some embodiments, only a single fiber bundle is used, but it is to be understood that a serially-arranged fiber bundle solution may also be suitable. In other embodiments, one or more bundles may be combined with further components, such as a light guide or guides. Discussion of exemplary fiber/light guide combinations can be found in co-pending U.S. patent application entitled "Speckle Reduction Using a Fiber Bundle and Light Guide," Ser. No. 11/503,859, filed Aug. 14, 2006 published as US20080037933A1 on Feb. 14, 2008, which is incorporated by reference herein for all purposes in its entirety to the extent it is not in conflict with the present subject matter.

From the output termination of the fiber bundle 1021, the laser beam is imaged by means of illumination transfer lenses 1301, 1302 onto the objective lens in use 1201, which is operative to focus the illumination onto a wafer 1100 being inspected. Appropriate alternative objective lenses 1201' can be swung into place on an objective revolver 1200, as is known in the microscope arts. The illumination returned from the wafer is collected by the same objective lens 1201, and is deflected from the illumination path by means of a beam splitter 1202, towards a second beam splitter 1500, from where it is reflected through the imaging lens 1203, which images the light from the wafer onto the detectors of the imager, with one of the detectors represented in FIG. 10 at 1206. In this example, only a single detector and optical path is shown for purposes of example. In practice, the path of light comprising the split portions of the inspection image will, of course, vary according to the state of the tool, detector arrangement, etc. In this example, the second beam splitter 1500 is used to separate the light going to the imaging functionality from the light used in the auto-focus functionality, which is directed by means of the auto-focus imaging lens 1501 to the auto-focus detector 1502.

When conventional dark field illumination is required for the imaging in hand, a dark field side illumination source 1231 is used to project the required illumination beam 1221 onto the wafer 1000. When orthogonal dark field, or obscured reflectance dark field illumination is required for the imaging in hand, an alternative dark field illumination source 1230 is used to project the required illumination beam 1232 via the obscured reflectance mirror 1240 onto the wafer 1000 orthogonally from above. FIG. 10 indicates sources 1300, 1231, and 1230 at different locations. However, any or all of sources 1300, 1230, and 1231 may comprise the same light source, with the bright field, dark field, and obscured reflectance dark field effects achieved through moving the source(s) and/or redirecting illumination to the appropriate angle using one or more optical components. Further, it is to be understood that other arrangements for laser illumination and/or other illumination methods entirely could be used in conjunction with the present subject matter.

In operation, one or more images of the wafer are obtained and the images are analyzed to determine the presence or absence of a defect or potential defect in the wafer. For example, the tool may include an image analysis system comprising one or more computers or other suitable image processing hardware configured to evaluate the images. In the example of FIG. 9, an image processing system 99 includes parallel configured image processing channels 90 for image grabbing by an image grabber 92, an image buffer 94, a defect detection unit 96, a defect file 98, and control/data links 101. Image data acquired by focal plane assembly 30 featuring twenty-four two-dimensional CCD matrix photo-detectors 52 is processed in parallel, whereby each of the twenty-four CCD matrix photo-detectors 52 communicates separately, in parallel to the other CCD matrix photo-detectors 52 of focal plane assembly 30, with image grabber 92, via twenty-four separate image processing channels 90. Instead of processing image data using a single serial channel of 48 megapixels at a CCD frame speed acquisition rate of 60 times per second, resulting in a single channel with a very high, 3 gigapixels per second processing rate, each of the twenty-four separate image processing channels 90 having about 2 megapixels of image data, acquired at a rate of 60 times per second, is used for processing at a moderate rate of tens of megapixels per second. Image processing system 99 is in communication with central control system 20 via control/data links 102

As another example, the tool may be connected to suitable hardware for image analysis, or image data may be provided to such hardware in any other manner.

Any suitable type(s) of analysis may be used to determine the presence or absence of defects. For example, the tool may obtain images on a frame-by-frame basis and compare single frames or groups of frames to references. As another example, the tool may analyze images without comparison to other images, such as locating bright spots on a dark area and/or dark spots on a light area. Any suitable comparison/analysis technique(s) may be used, including cell-to-cell comparison, die-to-die comparison, and may be carried out using any suitable software algorithm(s) and/or specialized hardware to analyze and process the images.

The above discussion is for purposes of example only with regard to illumination and imaging techniques. The present subject matter can be utilized in the context of any suitable inspection tool. Next, several different embodiments of detector arranging techniques will be discussed.

Figure 1A:
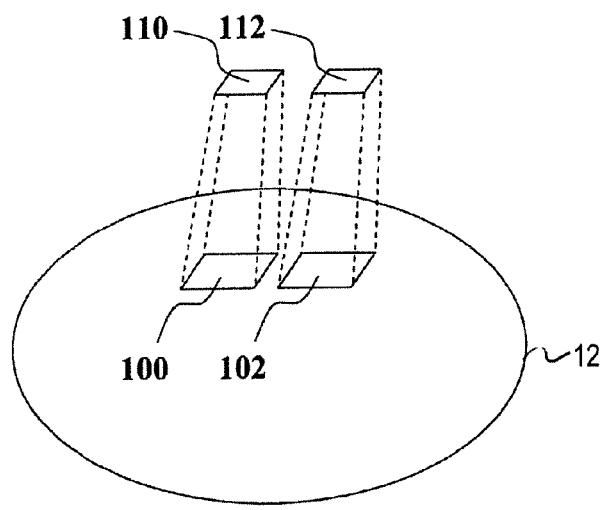
FIG. 1A shows the ultimate relationship between detectors and imaged object locations when a tool is operating in a "multiple location state"

FIG. 1A illustrates an example of imaging performed using two detectors when a tool is operating in the "multiple location" state. In this figure, two locations on the article (100 and 102) are imaged by two different respective detectors 110 and 112.

The imaging optics between the article and the detectors are not illustrated and may be any suitable arrangement of optical components. For example, arrangements in accordance with one or more aspects of the examples described in the following sections can be used. Although several examples herein pertain to two detectors, it should be understood that more than two detectors may be used.

Figure 2A:
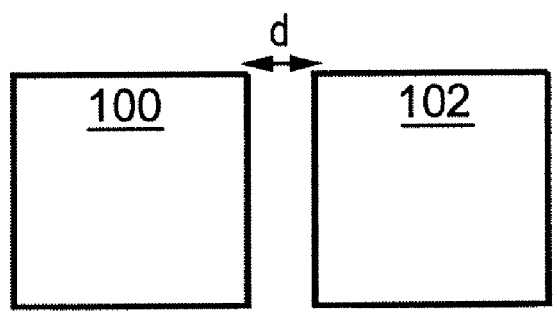
FIG. 2 illustrates, at (A), (B), and (C), examples of the relative positioning of imaged areas of an object.
Figure 2B:
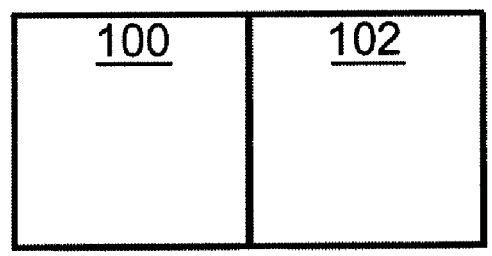
Figure 2C:
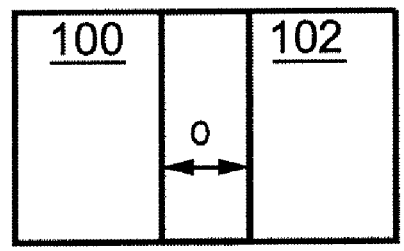

FIG. 2 provides some examples of the relative positioning of locations 100 and 102. For example, the locations on the article may be spaced in one or more directions, such as shown in FIG. 1A and in FIG. 2A, where the locations are separated by a distance "d." In some embodiments, the locations are adjacent as shown in FIG. 2B, while in some embodiments, the locations at least partially overlap as shown at "o" in FIG. 2C.

In some embodiments, when locations are separated by a space, the space may be an integer multiplication of the detector size, and particularly may be an even integer multiplication of the detector size. However, in other embodiments, the spacing between locations is any size. Further, not all locations need to be equally spaced or oriented to one another in the same manner. Additionally, the spacing of detectors may or may not correspond to the spacing of the imaged locations.

Figure 3:
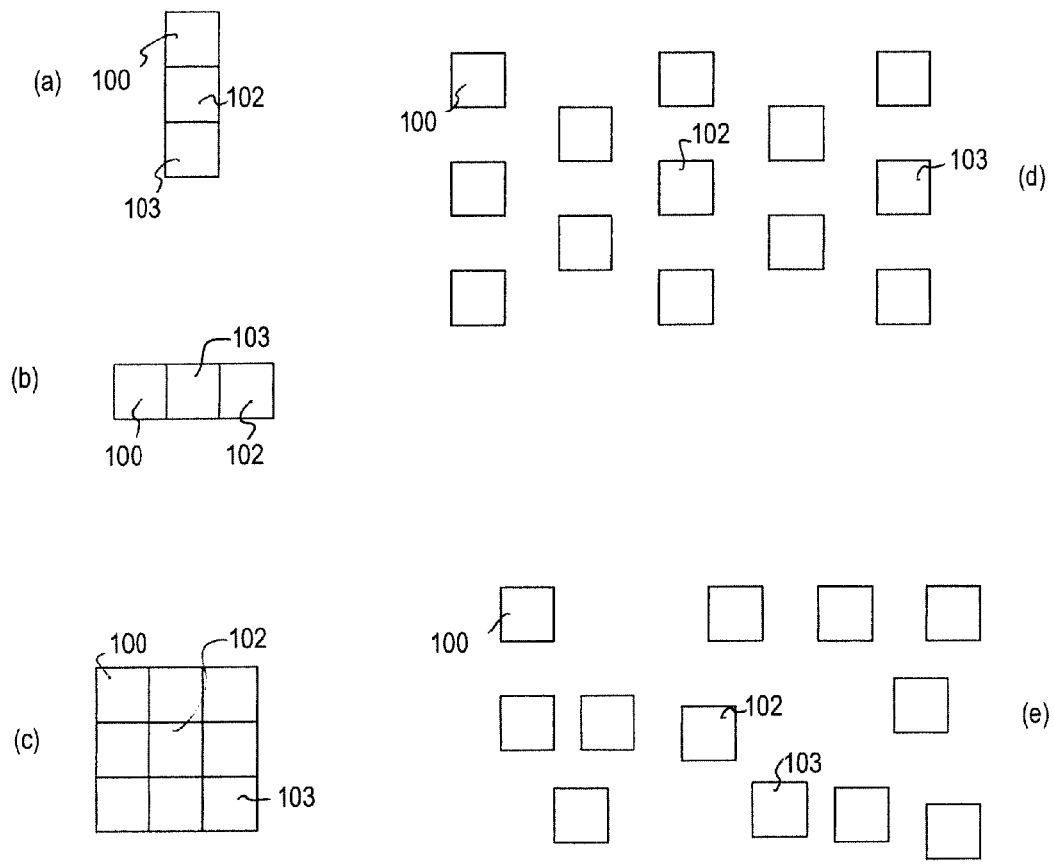
FIG. 3 is a diagram showing several examples of the relative positioning of imaged areas of an object.

The locations that are simultaneously imaged on the article at may be arranged in any suitable way, including different spacings in the horizontal and vertical direction (with "horizontal" and "vertical" referring to perpendicular directions relative to the plane of the wafer or other article being imaged). FIG. 3 provides several non-limiting examples such as: the vertical array shown at (a) in which locations 100, 102, and 103 are arranged vertically; the horizontal array shown at (b) in which locations 100, 102, and 103 are arranged horizontally; a two-dimensional dimensional array shown at (c) in which locations 100, 102, and 103 are part of an array of other locations. The locations may be spaced, such as the alternating horizontal or vertical arrays shown at (d). Any arbitrary arrangement, and example of which is shown at (e), can be used as well.

The different locations may be spaced apart in the same plane on the article. However, in some embodiments, different locations are additionally or alternatively spaced apart so as to lie in different planes. For example, detectors may be positioned relative to the focal plane of the imaging lens (es) used to image the object. Thus, the detected locations may overlap horizontally and/or vertically while the detectors nonetheless view different parts of the article, such as different layers.

It is also possible to achieve overlap without varying the detector position, so that different parts of different detectors may view the same location on the article. For example, two different detectors may view the image in different magnification.

Figure 1B:
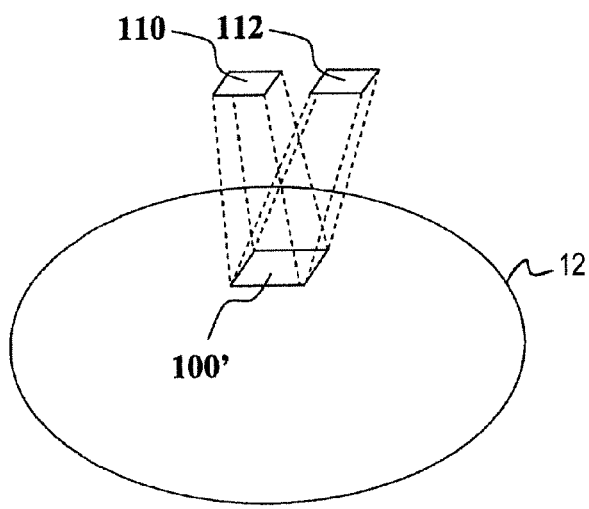
FIG. 1B shows the ultimate relationship between detectors and imaged object locations when a tool is operating in an exemplary "multiple imaging state"

FIG. 1B illustrates how an object is imaged by detectors in a tool operating in a "multiple imaging" state. In this figure, a single location 100' on the article is imaged by two different detectors 110 and 112. These are the same detectors used for imaging when the tool is operating in the "multiple location" state, but in this example, the detectors are operating in different imaging modes from one another. In the particular example illustrated in FIG. 1B, the detectors are shown to operate using different collecting angles.

The imaging optics between the article and the detectors are not illustrated and may be any suitable optics, for example as described in the next sections. In addition, more than two detectors may be used, of course In some embodiments, not all detectors that are used in the multiple location state are used in the multiple imaging state. Similarly, some of the detectors that are used in the multiple imaging state may not be used in the multiple location state. Preferably, though, all the detectors used in the multiple location state are used in the multiple imaging state, and all the detectors used in the multiple imaging state are used in the multiple location state.

The different imaging modes may comprise any known kind of imaging mode, for example, but not limited to the following mode differences:

Different collecting angles: Multiple detectors view the same location on the article using different collection angle range (or ranges). The angle range(s) may be totally different or overlapped. In some embodiments, the angle range of one detector may totally contain or may totally be contained in an angle range of another detector.

Different polarization: Multiple detectors view the same location on the article using different polarizations. In some embodiments, the polarizations of detectors viewing the same area are orthogonal.

Different wavelength band: Multiple detectors view the same location on the article but with different wavelength range (or ranges). The wavelength range(s) may be totally different or may overlap. The wavelength range of one detector may totally contain or be contained in a wavelength range of another detector (i.e. one detector may detect a sub-range of a range of wavelengths detected by another detector). Use of a tool supporting "multiple imaging state" operation may be especially useful when using broadband or multiband (multiple wavelengths) illumination and/or imaging is desired. For an example of a tool using broadband or multiband radiation, see U.S. patent application Ser. No. 11/684, 191, published as US20070273945A1 on Nov. 29, 2007, which is incorporated by reference herein in its entirety for all purposes to the extent it is not in conflict with the present subject matter. Broadband or multiband wavelengths can be produced by broadband or multiband illumination or due to fluorescence or other non-linear phenomena. Instead of wavelength range, a single wavelength may be used, for all or at least one of the detectors.

Different attenuation: Multiple detectors view the same location on the article after different attenuation. In some embodiments, one "attenuation" is actually null attenuation. Imaging based on light that has been attenuated differently may be used for enhancing the dynamic range of the system.

Different focusing: Multiple detectors view the same location on the article but with different focusing position relative to the article plane. For example, the focus position for one detector may be beneath the article surface while another detector's focus position is on the article surface or above it. By using different focusing, different detectors may be sensitive for different layers on the article, and this may allow different detectors to be used to observe different types of defects.

Of course, the different imaging modes noted above may be used in combination. For example, a tool may support a multi-imaging state where a plurality of detectors view the same location, with the detectors viewing different wavelength ranges and at different focusing from one another.

The tool may support different imaging modes while in the multiple location state. For example, as noted above, the detectors in FIG. 1A image different locations. Detector 110 may have a different attenuation from detector 112 if, for example, a different dynamic range is needed to inspect area 100 as compared to area 102.

As another example embodiment of a multiple imaging state, two (or more) detectors may view the article in the same imaging mode. This may provide an advantage by reducing the noise, such as by using averaging or other operator between the data from the detector.

In addition to or instead of using different imaging for each detector, a multiple imaging state may be implemented by configuring the tool to provide different illumination for different detectors. For instance, in some embodiments, the different illumination can be applied at different times (preferably with a very short period between them) for different respective detectors. The detectors are opened to receive illumination (by electronic gating for example) or otherwise rendered operable to image the article only at the time of corresponding illumination.

Next, three different exemplary implementations of an inspection apparatus that supports operation in both a multiple location state (or states) and in a multiple imaging state (or states) are described. Specifically, examples of optical configurations are shown. In these examples, optical components and/or detectors are arranged so that the optical path to the detectors and/or the components of the light traveling along the optical path can be managed.

Figure 4:
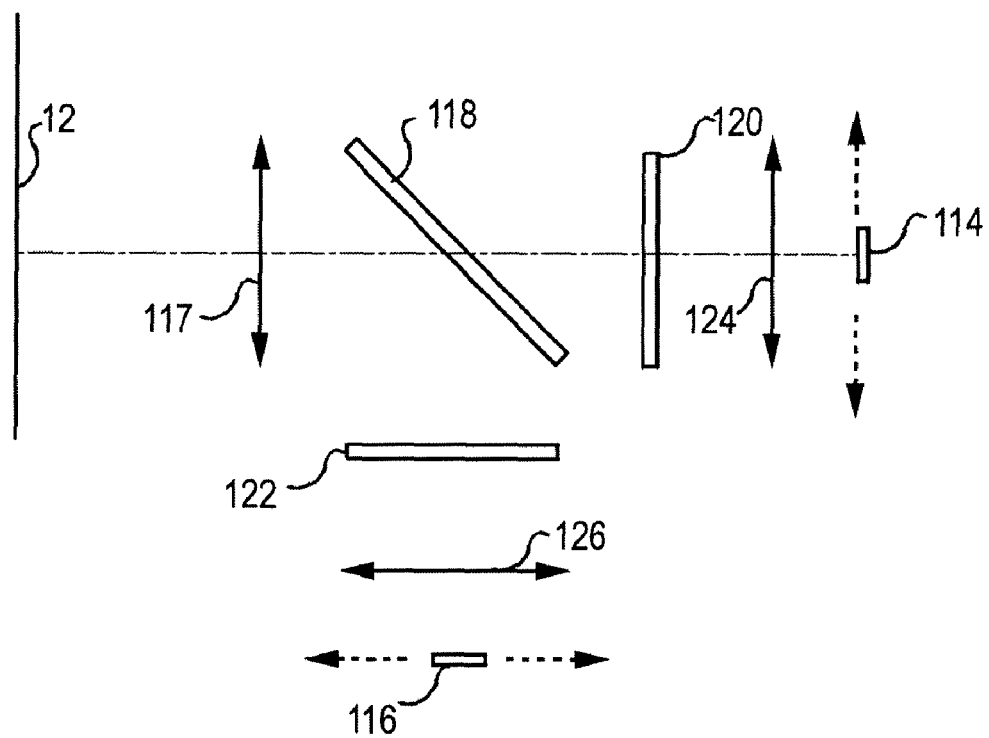
FIG. 4 generally illustrates an example of a set of variable optics that can be used in an inspection tool supporting multiple operating states.

FIG. 4 illustrates an example of an embodiment that can be used in a tool so that the tool supports "flexible states." In this embodiment, a beam splitter 118 is located in the imaging path between the article 12 and the detectors 114 and 116. The imaging path includes focusing lens 117. For example, the optics shown in FIG. 4 could be used to configure a replacement for optics 18 noted above with regard to FIG. 9, in which focusing lens 117 could correspond to focusing lens 46, imaging lenses 124, 126 would correspond generally to lens 42, and so on. Beam splitter 118 splits part of the image toward Detector 114 and the other part toward Detector 116. Preferably, the beam splitter is 50% transmitting and 50% reflecting, although other percentages could be used in other embodiments.

A changeable filter 120 is located in the imaging path of detector 114 and another changeable filter 122 is located at the imaging path of detector 116. These filters are used to change the imaging mode of each detector. After each filter, a focusing lens 124 and 126 images the light onto detectors 114 and 116, respectively.

In this example, the two detectors are adjustable, e.g. the location of each detector can be changed up, down, left or right in the corresponding focal plane of its focusing lens. The detectors may be additionally movable perpendicular to the focal plane to move the focus point below or above the article. For example, the detectors may be housed or mounted on tracks or other assemblies which allow the detector location to be varied either manually or via suitable control signals from the inspection tool. The detectors may be moved in any number of directions along straight and/or curved paths as needed.

Multiple Location State

Figure 5A:
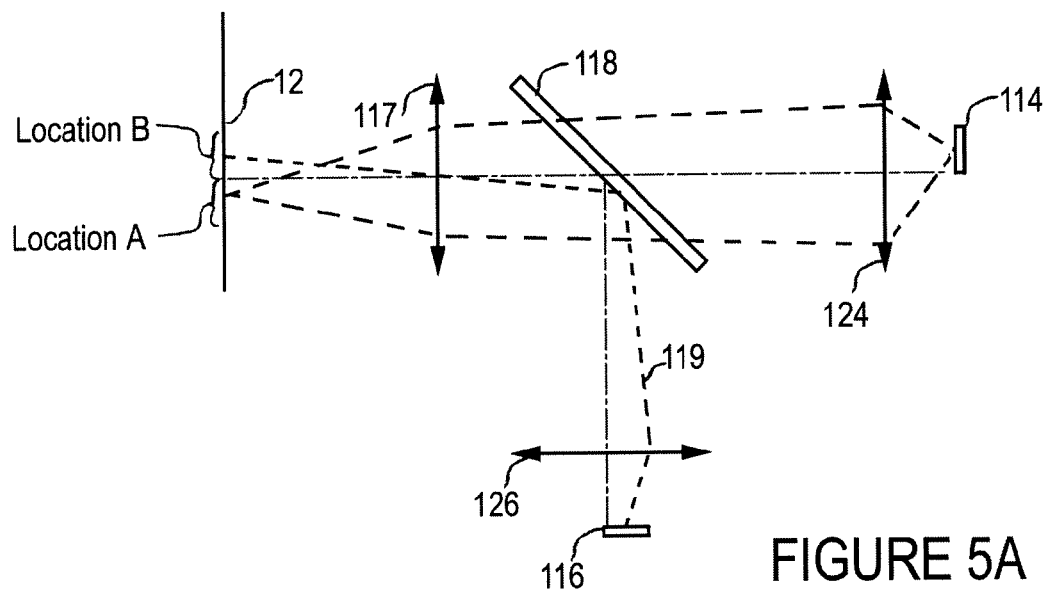
FIG. 5A shows the optics of FIG. 4 as configured when a tool is operating in a multiple location state.

The detector arrangement of FIG. 4 may be operated in the multiple location state as illustrated at FIG. 5A. When the tool is commanded to operate in this state, Detector 114 views Location A on article 12 and Detector 116 views Location B on the article. To execute this state, each detector is moved toward a pre-determined position so it will view the corresponding location on the article. Changeable filters 120 and 122 are pulled out or neutralized during this state.

As with the detectors, the filters may be mounted on tracks or assemblies so that the filters can be physically moved (manually or automatically) to adjust the tool state. However, Changeable Filter 120 and/or 122 may remain in place, but may otherwise be adjusted so as not to affect light passing through. Accordingly, those filters are not shown in FIG. 5A.

The reflected light from Location A on the article is passed through lens 117 and transmitted partially by the beam-splitter 118 (the part reflected by the beam splitter is not illustrated). After the beam splitter, the light is focused on Detector 114 by lens 124. The extreme rays for Detector 114 are drawn as wide dashed lines.

The reflected light from Location B on the article is also passed through lens 117 and reflected partially by the beam-splitter 118 (the transmitted part is not illustrated). After the beam splitter, the light is focused on Detector 116 by lens 126. The middle ray for Detector 116 is drawn as a narrow dashed line and is indicated at 119 for purposes of clarity.

Multiple Imaging State

Figure 5B:
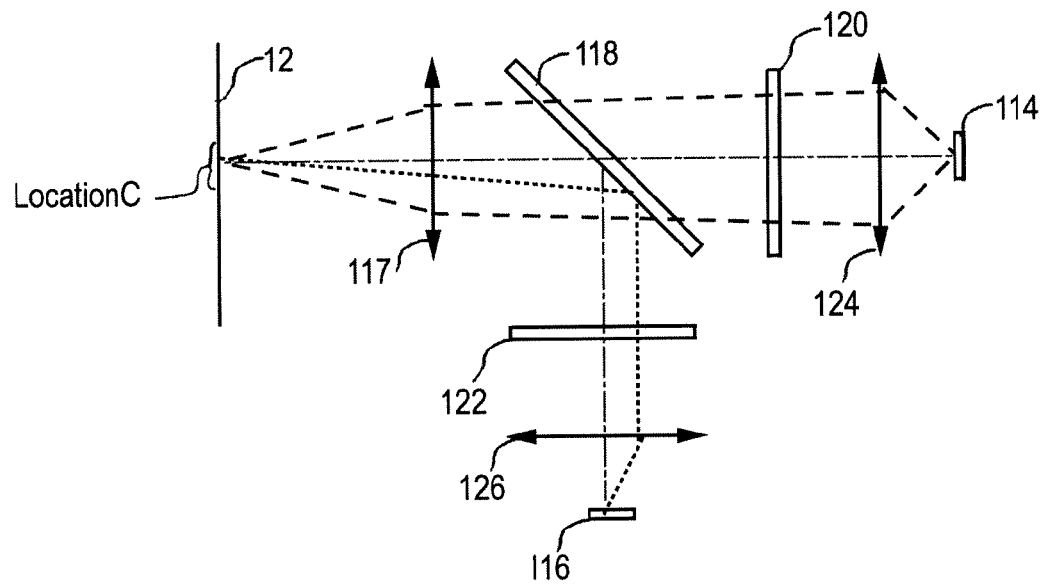
FIG. 5B shows the optics of FIG. 4 as configured when a tool is operating in a multiple imaging state.

The multiple imaging state is illustrated at FIG. 5B. In this example, in the multiple imaging state, both detectors (Detector 114 and Detector 116) view the same location (Location C) on the article. To execute this state, each detector is moved so it will view Location C on the article, and the changeable filters 120, 122 are put in place or activated. In this example, detectors 114 and 116 are moved toward the central position. It will be understood, though, that the particular direction(s) of movement will depend on the original detector locations and desired location for viewing.

Changeable filters 120, 122 may comprise any suitable type of filter which can be used to determine the resulting mode of the detector(s) receiving light that has passed through the filter. The term "changeable" is intended to encompass variable filters whose characteristics can be adjusted in-place, but also to include fixed filters whose functionality can be changed by physical moving the filter (such as by changing the filter position and/or orientation). Thus, changeable filters can include, but are not limited to:

Spatial mask: a spatially changeable filter is located at the Fourier plane of 117. This mask can be used to determine the collection angles of each detector. Similarly, the same kind of filter can be located at the Fourier plane of L2.

Polarizers, retarders (e.g., λ/2 plate) or combination thereof: These may be used to determine the polarization of light impinging each detector.

Spectral filters: These may be used to determine/control the wavelength or wavelength bands each detector views.

Attenuators: these may be used to determine the attenuation of the light impinging each detector.

Focusing Element: Any suitable optical element (such as, for example, flat plates or lenses) can be used to change the focus position.

Any of the above may be used in conjunction with one another or any other suitable filtering mechanism to adjust the mode of the respective detector.

The reflected light from Location C on article 12 is passed through lens 117 and transmitted partially by the beam-splitter 118 and reflected partially from it. The transmitted light is filtered by Changeable Filter 120, and focused on Detector 114 by lens 124. The extreme rays for Detector 114 are drawn as wide dashed lines.

The reflected light is filtered by Changeable Filter 122, and focused on Detector 116 by lens 126. The middle ray for Detector 116 is drawn as a narrow dashed line.

As mentioned above, the changeable filters can be configured in any suitable way so as to control their use and effects on light in the optical paths. For example, the filters may be fixed filters or masks. Changing the imaging state is achieved by placing the filter/mask in the optical path or taking it out. As another example, the filters may be mechanically changed. The imaging state is changed mechanically, such as by rotating a polarizer. As another example, the filters may be electronically or electro-mechanically changed. In such filters, the imaging is changed by using an LCD mask or micro shutters array as the spatial mask in the focal plane.

In addition to the lenses 124, 126, other components may be added between the changeable filter(s) and their respective detectors, such as polarizers, attenuators, spectral filter, etc that are same or different for each optical path. The components may be added before the focusing lenses, after the focusing lenses, or combined with the focusing lenses (for example, a focusing lens with high light absorption may serve as an attenuator as well).

FIGS. 5A and 5B each are a simplified diagram, and it will be understood that, in some embodiments, 117 and/or 124 and/or 126 may comprise more complicated optics, such as, for example, multiple lenses, doublets, triplets, etc. One or more components of the optics may contain diffractive lenses or graded index lenses.

Part or all of the different imaging may be implemented by repositioning or reconfiguring beam-splitter 118 instead of or in addition to changing the changeable filters. For example, a polarizing beam splitter may be placed after 117 instead of using polarizers as the changeable filter.

As another example, the beam splitter may be highly reflective and low transmissive. The detector receiving the transmitted rays would not need an attenuator in such a case. Of course, the beam splitter could by highly transmissive and lowly reflective to reverse the situation.

As another example, instead of using spectral filters, a dichroic beam splitter could be used. Generally speaking, beam splitter characteristics can be changed in any suitable manner to adjust the imaging mode in addition to, or instead of, using the changeable filters.

In this example, light was split to two detectors. Of course, light can be split to more than two detectors using cascaded beam splitters, combination of beam splitters and mirrors, and/or any suitable splitting system.

One Lens/Two Lenses Embodiments

Figure 6A:
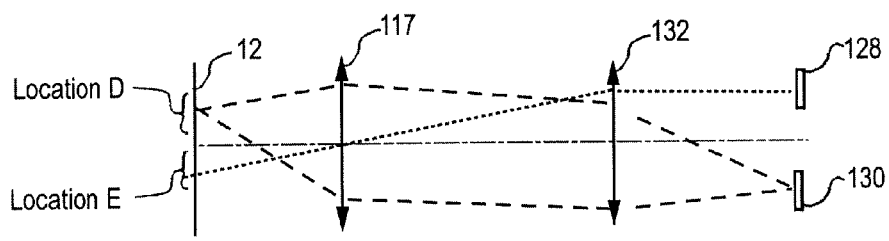
FIG. 6A is another exemplary arrangement of variable optics, showing a configuration in a tool operating in a multiple location state.
Figure 6B:
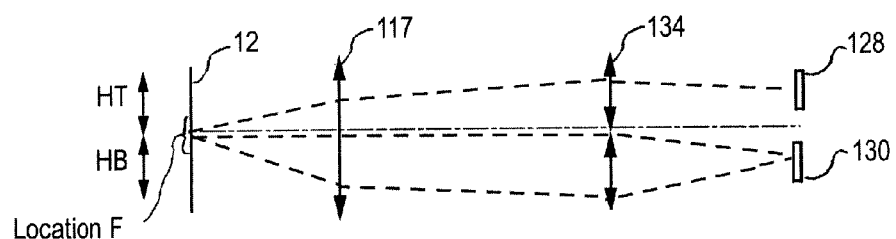
FIG. 6B is showing a variation of the optics of FIG. 6B when the tool is operating in a multiple imaging state.

A second exemplary embodiment is illustrated in conjunction with FIGS. 6A and 6B. In this example, a tool supports a multiple location state and a multiple imaging state in which a different collection angle is used for each detector. The two different states are exchanged by switching a single lens 132 for an optic element 134 containing or functioning as multiple lenses. In this example, optic element 134 contains two lenses, and the illustrated switch uses two detectors.

In the multiple location state (FIG. 6A) different locations on article 12 (Location D and Location E) are imaged on respective detectors 128 and 130.

Rays from the Location D of the article, for example, go through lens 117, and are focused by single lens 132, which is positioned on the Fourier plane of lens 117, onto Detector 130. Similarly, rays from Location E are focused on Detector 128.

In the multiple imaging state, the tool's optics are configured as shown in FIG. 6B. Location F of article 12 is imaged on two detectors 128 and 130 in two ranges of collection angles. This imaging state is implemented by exchanging single lens 132 for an optical element 134.

Optical element 134 comprises two adjacent lenses, each with a power equal the power of lens 132. Discrete lenses may be used, or optical element 134 may comprise any suitable material configured to function as multiple lenses. All the rays that reflected from horizontal to bottom direction (HB in FIG. 6B) are imaged by 117 and the bottom lens of element 134 to Detector 130. All the rays reflected from horizontal to top direction (HT in FIG. 6B) are imaged by 117 and the top lens of element 134 to Detector 128.

The lenses comprising element 134 may be arranged in any size or order. FIG. 7 illustrates several exemplary configurations of element 134 when a pair of lenses is used. In FIG. 7, the aperture of single lens 132, which is replaced by element 134 when the tool is in the multiple imaging state, is represented by a dashed line 136. In the example illustrated at FIG. 7A, the two lenses (I and 11) are side by side, and each of them is a different half of the total aperture. In the example illustrated at FIG. 7B, the two lenses are circular, and each lens is half of the diameter of lens 132. In this case the two lenses are also positioned adjacent to one another.

Figure 7A:
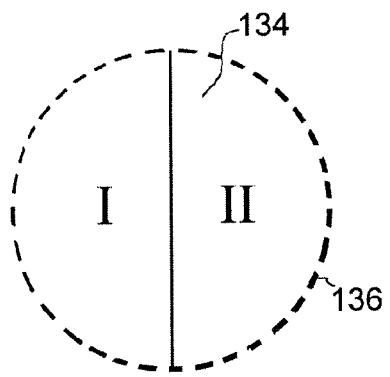
FIGS. 7A, 7B, 7C, and 7D are example configurations of an optical element comprising or functioning as multiple lenses.
Figure 7B:
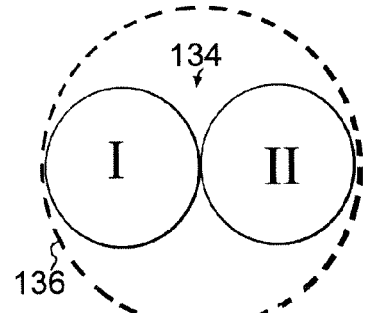
Figure 7C:
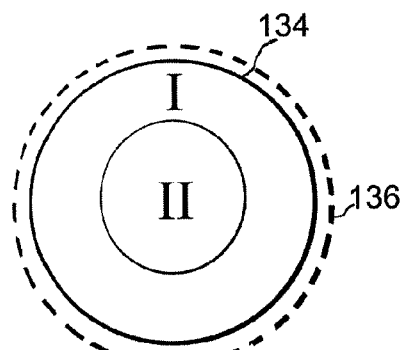

In the example illustrated at FIG. 7C, one lens is larger than the other, in this example, equal to or almost equal to the original size of single lens 132. The larger lens (I) comprise a hole in which the second lens (II) is placed. This configuration may require wedges or other optics to direct the light to the detectors.

Figure 7D:
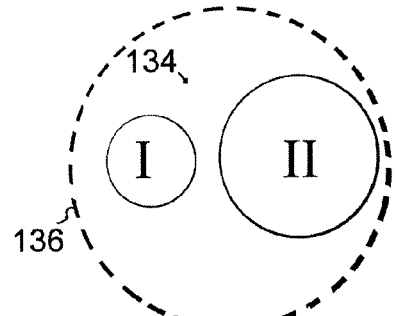

In the example illustrated at FIG. 7D, non adjacent lenses are shown. Additionally, the lenses have different sizes from one another.

Changing Objective Embodiment

Figure 8:
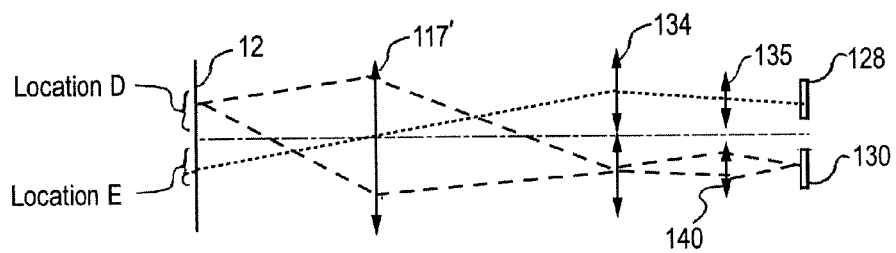
FIG. 8 shows another exemplary arrangement of variable optics, showing an alternative configuration for a tool operating in a multiple location state and using an arrangement shown in FIG. 6B when in the multiple imaging state.

FIG. 8 illustrates a configuration of optics in which a multiple location state is achieved by changing the objective lens 117. The multiple imaging state of this embodiment is same as the multiple imaging state of the second embodiment of FIG. 6B. However, in this embodiment, the same optical element 134 used in the multiple imaging state is also used in the multiple location state.

In contrast to the multiple location state of FIG. 6A, though, in this embodiment, a different objective lens 117' is used instead of 117 when the tool is operating in the multiple location state. Additionally, relay lenses 135 and 140 are placed in the optical path of each respective detector 128, 130 as shown in FIG. 8.

In this state, Location E is first imaged on the top lens of element 134. This lens and the nearby relay lens 135 image location E on Detector 128. Similarly, Location D is imaged onto Detector 130 via 117', the bottom lens of element 134, and a corresponding relay lens 140.

In this embodiment, the two detectors may image adjacent areas on the article without shadows between them. For examples of imaging adjacent areas on the article without shadows, see U.S. patent application Ser. No. 11/944,684, entitled "Image Splitting in Optical Inspection Systems" by Dov Furman, Shai Silberstein, Effy Miklatzky, Daniel Mandelik, and Martin Abraham, filed Nov. 26, 2007 and published as US 2008-0137074 A1, which is incorporated by reference herein in its entirety for all purposes to the extent it is not in conflict with the present subject matter.

In various embodiments, 117' may be placed at a different position than 117; 117' may have a different power from 117; or 117' may be both placed at a different position and may have a different power from 117.

To implement the multiple imaging state, in addition to the element 134, other components may be added, such as polarizers, attenuators, spectral filter, etc that are same or different for each lens in element 134. The components may be added before the lenses, after the lenses, or combined with the lenses (for example, a lens with high light absorption may be served as an attenuator as well).

The components may be added also before, after or in combination of the relay lenses if/when relay lenses are used. 117 and/or 132 and/or the relay lenses 135, 140 may be more complicated optics and may comprise, for example, multiple lenses, doublets, triplets, etc. Further, one or more components of the optics may comprise diffractive lenses or graded index lenses.

In some embodiments, instead of two lenses in element 134 for two detectors, more than two lenses and respective detectors may be used. For example element 134 may comprise three lenses for imaging three parts on the article to three detectors in the multiple location state, while in a multiple imaging state, three ranges of collection angles are imaged to the three detectors.

Although not shown in FIG. 8, a wedge may be placed after each lens of 132 or element 134 in order to direct the output from the lens to a specific detector.

The detector(s) used in an optical inspection tool can comprise any suitable number, type, or combination of light-sensing elements. The underlying sensing can be based on any suitable technology. For instance, in various embodiments, one or more of the following types of detector types can be used: CCD, CMOS, PMT, and/or avalanche photodiode detectors.

The detectors may be of any suitable type. For example, one or more detectors may comprise an area detector, such as a matrix of photo-sensors producing 2 dimensional image data. As another example, one or more detectors can comprise a TDI line detector, i.e. a matrix of photo-sensors which produces 1 dimensional image data. As another example, one or more detectors can comprise a line detector i.e. a line of photo-sensors which produces 1 dimensional image. In certain embodiments, a detector can comprise a "point detector," where each detector signal represents a pixel.

It will be appreciated that, in some embodiments in which light sensing and imaging is based on point detection, such as when PMT and/or avalanche photodiode detectors are used, the illumination and/or imaging hardware will need to be varied appropriately from the example arrangements discussed above in conjunction with FIGS. 9 and 10. For example, embodiments of a tool using PMT and/or avalanche photodiode detectors can include some sort of scanning mechanism to variably illuminate spots on the wafer or other object(s) under inspection. For instance, a suitable illumination source (such as an argon laser or another laser) can be used in conjunction with an acousto-optical deflector to scan one or more illuminating beams across the wafer or other object(s) under inspection.

As one example of inspecting using a scanning source, a sawtooth pattern in the time domain can be used while the stage moves the wafer orthogonally to the movement of the illuminating beam. The imaging optics can be arranged to appropriately collect light from the illuminating beam as reflected or otherwise scattered by the wafer. Exemplary details of an inspection system including a scanning illumination source can be found in U.S. Pat. No. 5,699,447, which is incorporated by reference herein in its entirety to the extent it does not conflict with the present subject matter. Exemplary discussion of line detection can be found in U.S. Pat. No.

6,724,473, which is incorporated by reference herein in its entirety to the extent it does not conflict with the present subject matter.

When TDI or line detection is used, illumination and relative movement of the wafer should be adjusted accordingly, with the image acquisition hardware/software also suitably configured. For instance, as is known in the art, when TDI detection is used, continuous illumination is applied while the imaging location on the wafer or other object is varied.

Similarly, the hardware/software used for image acquisition/analysis should be appropriately configured for embodiments in which point detection is used. Namely, rather than capturing an entire field of view instantaneously, the imaging hardware images a series of points (which may each comprise one or more pixels) from which the entire image of the wafer can be constructed. In some embodiments in which point detection is used, in the multiple-location state, the tool images multiple points at a given time, while in the multiple imaging state, a given point is imaged by multiple detectors (e.g. two or more point detectors operating in different imaging modes from one another).

In some embodiments, a tool using more than two detectors supports selection between two of the following three states: (1) All the detectors view a different respective location on the article; (2) All the detectors view the same location on the article, but with different imaging modes; and (3) Some of the detectors view the same location with different imaging, while some detectors view different locations from one another.

Preferably in some embodiments, the number of imaging modes in option (3) is the number of detectors divided by the number of viewed locations. In each viewed location, the same image is used for each mode. Thus, a tool could switch between operating in a purely multiple-location state to a mix of multiple locations and multiple modes, for example.

For example, if there are four detectors, the tool can image two different locations at a time while in the multiple imaging state, with each location imaged using two different modes. For instance, the detectors may be assigned as follows: Detector 1—Location I, imaging mode I; Detector 2—Location I, imaging mode II; Detector 3—Location II, imaging mode I; Detector 4—Location II, imaging mode II. Of course, this example may represent a subset of many available detectors and modes.

As another example, a tool with twenty-four detectors may support a "multiple imaging state" in which the tool can image eight different locations simultaneously in three modes.

The inspected article may be any article used in or resulting from a semi-conductor manufacturing process, such as wafers, masks, photomasks and reticles, although the principles discussed herein could be applied to inspection tools regardless of the article under inspection.

In some embodiments, when the detectors view different respective locations on the article, a different imaging mode for each detector may also be used. For example, between two detectors, Detector I may view location I in imaging mode II while Detector II views location II in imaging mode I.

The imaging state of the tool may be changed during an inspection, and not only before inspection, to use the best state for each part of the article. As an example, in a tool with four detectors supporting two different modes, the tool may operate in a multiple imaging state when high sensitivity is needed for some areas of a wafer and image two locations simultaneously in two different modes for each location. In other parts of the wafer where less sensitivity is needed, all four detectors may be used to image different respective locations in a single mode and thereby increase throughput. As mentioned above, while the detectors image different respective areas, the detectors may all operate in the same mode, or one or more detectors may image their respective area(s) in different modes from one another.

In some embodiments, it may be advantageous to change the state in between slices, i.e. after each slice (with a "slice" referring to an inspected section of the article along an imaging axis from start to end). However, if applicable, the states can be changed within inspection of a slice. In any event, the inspection tool can be configured to select appropriate inspection paths, sequences, and the like and thereby address changes in the size, shape, and coverage of its field of view in different states.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

The invention claimed is:

1. A semiconductor electro-optical inspection system comprising:
    a light source configured to illuminate an object under inspection;
    at least two detectors, each detector operative to generate an image of the object under inspection from light received from the object; and
    a set of variable imaging optics positioned on an optical path between the object under inspection and the at least two detectors;
    wherein the system is configured to selectively operate in at least:
        (i) a first state, in which each of at least two different physical locations on the object under inspection are imaged by a respective detector, and
        (ii) a second state, in which at least two different detectors image the same physical location on the object under inspection using different imaging modes from one another.

2. The system set forth in claim 1, wherein at least some of the detectors are repositionable and the system is configured to reposition the detectors when changing between the first state and the second state.

3. The system set forth in claim 2, wherein:
    the set of variable imaging optics comprises a plurality of changeable filter elements and a splitting apparatus;
    in the first state, the splitting apparatus directs light corresponding to different physical locations of the object under inspection along different optical paths, each different optical path leading to the respective detector; and
    in the second state, the changeable filter elements are each positioned in a respective optical path after the splitting apparatus so as to change the imaging mode of the at least two different detectors in the path.

4. The system set forth in claim 3, wherein at least one changeable filter element comprises a spatial mask, a polarizer, a spectral filter, an attenuator, or an element that changes the focus position above, on, or below the focus point on the object under inspection.

5. The system set forth in claim 1, wherein:
    the set of variable imaging optics comprises an optical element comprising multiple lenses, the optical element selectively exchangeable with a post-objective lens and placed in a position after an objective lens in the optical path;

the post-objective lens is configured to focus light from different physical locations on the object under inspection to at least two respective detectors and is positioned in the optical path during the first state; and the optical element comprising multiple lenses is placed in the optical path during the second state so that the at least two different detectors image the same physical location on the object under inspection using different collection angles.

6. The system set forth in claim 5, wherein the optical element comprising multiple lenses comprises a single optical element having at least two portions that act as different lenses.

7. The system set forth in claim 1, wherein:

the set of variable imaging optics comprises a first objective lens and a second objective lens that can be selectively positioned in the optical path before an optical element comprising multiple lenses;

the optical element comprising multiple lenses remains in the optical path during both the first and the second state;

during the first state, the first objective lens adjusts incoming light from the object under inspection so that at least two detectors image different respective locations on the object under inspection; and during the second state, the second objective lens passes incoming light from the object under inspection so that the optical element comprising multiple lenses passes light to different detectors and the at least two different detectors image the same physical location on the object under inspection using different collection angles.

8. The system set forth in claim 1, wherein:

the system comprises at least four detectors each operable to selectively image the object at least two modes;

in the first state, the system images at least four different locations on the object under inspection simultaneously; and in the second state, at least two locations on the object under inspection are imaged simultaneously in at least two modes.

9. The system set forth in claim 1, wherein:

the system comprises at least four detectors each operable to selectively image the object in at least two modes;

in the first state, the system images at least one location on the object under inspection simultaneously in two different modes.

10. The system set forth in claim 1, wherein:

the system comprises at least four detectors each operable to selectively image the object in at least two modes;

in the second state, at least one imaging mode is used to image at least two locations on the object under inspection.

11. The system set forth in claim 1, wherein:

in the second state, the light source is configured to illuminate the object under inspection multiple times; and the at least two different detectors used to image the same physical location on the object under inspection image the object under inspection at different respective times.

12. The system set forth in claim 1, wherein, when the system is operating in the second state, the at least two different detectors image the same physical location on the object under inspection using different collection angles.

13. The system set forth in claim 1, wherein, when the system is operating in the second state, the at least two different detectors image the same physical location on the object under inspection using differing polarizations.

14. The system set forth in claim 1, wherein, when the system is operating in the second state, the at least two different detectors image the same physical location on the object under inspection using different spectral bands.

15. The system set forth in claim 1, wherein, when the system is operating in the second state, the at least two different detectors image the same physical location on the object under inspection using different attenuations.

16. The system set forth in claim 1, wherein, when the system is operating in the second state, the at least two different detectors image the same physical location on the object under inspection using different focal positions relative to the object under inspection.

17. The system set forth in claim 1, wherein the at least two detectors comprise two-dimensional detectors.

18. The system set forth in claim 1, wherein the at least two detectors comprise TDI detectors.

19. The system set forth in claim 1, wherein the at least two detectors comprise line detectors.

20. The system set forth in claim 1, wherein the at least two detectors comprise PMT detectors.

21. The system set forth in claim 1, wherein at least one detector comprises an avalanche photodiode detector.

22. A method of inspecting an object in an electro-optical inspection system comprising a set of detectors, the method comprising:

illuminating the object;

imaging at least one location on the object in different modes by using at least two detectors of a first subset of the detectors to image the same location; and imaging at least two different locations on the object, with each location imaged using a respective detector of a second subset of the detectors;

wherein the first and second subsets at least partially overlap.

23. The method set forth in claim 22, further comprising:

repositioning at least some of the set of detectors between imaging the same location on the object in different modes and imaging at least two different locations on the object with the respective detector.

24. The method set forth in claim 23, further comprising:

when imaging at least two different locations with the respective detector, splitting light along different optical paths so as to direct the light from respective locations on the object to the respective detectors; and when imaging at least one location in multiple modes, positioning a plurality of changeable filter elements in the optical path leading to each detector to adjust the imaging mode of the detector.

25. The method set forth in claim 22, wherein light from the object is gathered using an objective lens and the method further comprises:

placing a post-objective lens configured to focus light from different physical locations on the object to the respective detectors when imaging at least two different locations each with the respective detector; and replacing the post-objective lens with an optical element comprising multiple lenses so that multiple detectors image the same physical location on the object at different collection angles when the post-objective lens is in place.

26. The method set forth in claim 22, further comprising:

selectively placing one of a first and second objective lens in the optical path before an optical element in the path comprising multiple lenses;

wherein, when the first objective lens is in the optical path, the first objective lens and optical element in the path comprising multiple lenses direct light from different locations on the object to the respective detectors, and when the second objective lens is in the optical path, the second objective lens and optical element in the path comprising multiple lenses direct light so that at the at least two different detectors image the same physical location on the object.

27. The method set forth in claim 22, wherein imaging comprises illuminating the object multiple times when using the at least two different detectors to image the same physical location on the object, the illumination timed so that the respective detectors can image the location at different times.

\* \* \* \* \*